(12) United States Patent
Gasser et al.

(10) Patent No.: US 7,686,837 B2
(45) Date of Patent: Mar. 30, 2010

(54) POLYAXIAL LOCKING IMPLANTABLE ORTHOPEDIC FIXATION DEVICE

(75) Inventors: André Gasser, Langendorf (CH); Christian Lutz, Solothurn (CH); Thomas Baumgartner, Derendingen (CH); Andreas Bernhard, Meinisberg (CH)

(73) Assignee: Stryker Trauma S.A. (CH)

( * ) Notice: Subject to any disclaimer, the term of this patent is extended or adjusted under 35 U.S.C. 154(b) by 112 days.

(21) Appl. No.: 10/544,323

(22) PCT Filed: Dec. 31, 2003

(86) PCT No.: PCT/CH03/00852

§ 371 (c)(1),
(2), (4) Date: May 15, 2006

(87) PCT Pub. No.: WO2004/069066

PCT Pub. Date: Aug. 19, 2004

(65) Prior Publication Data

US 2006/0241618 A1 Oct. 26, 2006

(30) Foreign Application Priority Data

Feb. 3, 2003 (CH) .................................. 150/03

(51) Int. Cl.
*A61B 17/58* (2006.01)
(52) U.S. Cl. ..................................... 606/287
(58) Field of Classification Search ............. 411/6, 411/24–28, 44, 45, 57.1, 60.2; 606/60, 63, 606/65, 66, 69–73, 319, 280–299, 61
See application file for complete search history.

(56) References Cited

U.S. PATENT DOCUMENTS

| 1,053,682 | A | * | 2/1913 | Van Antwerp | 411/60.2 |
| 1,356,401 | A | * | 10/1920 | Peirce | 411/24 |
| 1,852,089 | A | * | 4/1932 | Pleister | 411/24 |
| 2,443,466 | A | * | 6/1948 | Lord | 411/445 |
| 3,911,782 | A | * | 10/1975 | Liebig | 411/24 |

(Continued)

FOREIGN PATENT DOCUMENTS

DE 102 26 496 A1 1/2003

*Primary Examiner*—Thomas C Barrett
*Assistant Examiner*—Christopher Beccia
(74) *Attorney, Agent, or Firm*—Lerner, David, Littenberg, Krumholz & Mentlik, LLP

(57) ABSTRACT

The invention relates to an implantable orthopaedic device comprising a load-bearing element, such as a bone plate, for fixing elements, such as bone screws, that can be oriented polyaxially. The load-bearing element is equipped with at least one opening for the passage of the fixing elements. A two part insert is provided in the opening, the insert having an external form that complements the internal form of the receiving opening and permits the polyaxial rotation of the insert in the opening. The insert is equipped with a central bore for receiving the body of the fixing element. The first insert element part has a central inner hollow chamber, into which the second insert element part can be introduced. The first insert element is flexible or has at least one slit, in such a way that when the two insert elements are displaced axially in relation to one another, the first insert element in the plate can be expanded at least partially in order to block the position and alignment of the fixing element in the device in a polyaxial manner.

16 Claims, 4 Drawing Sheets

U.S. PATENT DOCUMENTS

| | | |
|---|---|---|
| 4,921,381 A * | 5/1990 | Gschwend et al. ............ 411/25 |
| 5,474,553 A | 12/1995 | Baumgart |
| 5,607,426 A | 3/1997 | Ralph et al. |
| 5,607,428 A | 3/1997 | Lin |
| 5,683,392 A * | 11/1997 | Richelsoph et al. ........... 606/61 |
| 5,954,722 A | 9/1999 | Bono |
| 6,030,389 A | 2/2000 | Wagner et al. |
| 6,235,033 B1 | 5/2001 | Brace et al. |
| 6,280,442 B1 * | 8/2001 | Barker et al. .................. 606/60 |
| 6,293,743 B1 * | 9/2001 | Ernst et al. .................... 411/24 |
| 6,454,769 B2 * | 9/2002 | Wagner et al. ................ 606/69 |
| 2001/0021851 A1 * | 9/2001 | Eberlein et al. ............... 606/69 |

* cited by examiner

POLYAXIAL LOCKING IMPLANTABLE ORTHOPEDIC FIXATION DEVICE The invention concerns an implantable orthopedic device with a load-bearing element, such as a bone plate, with at least one polyaxially-oriented fixation element such as a bone screw. In the load-bearing element there is at least one opening for the passage of the polyaxially oriented fixation element. A first insert is provided that can be inserted in the opening into a mounting, such that the insert exhibits an external shape that is complementary to the internal shape of the mounting. This allows a polyaxial rotation of the insert in the mounting. The first insert exhibits a central through-bore for receiving the body of the fixation element. In addition the implantable orthopedic device has a second insert for holding the first insert in the mounting.

An alternate device is known, for example, from U.S. Pat. No. 5,954,722. There is at least one opening provided in the plate that defines a mounting, in which a one-piece insert equipped with a slit going all the way through a wall thereof can be inserted. The insert has inner threading, in which a threading of the fixation element can engage. The opening of the plate is shaped like a partial hollow sphere, so that it forms a mounting for the insert which exhibits a spherical outer surface. In this way, the insert may be polyaxially oriented with a fixation element that is screwed into it. When the fixation element is screwed into the insert, it spreads the insert apart, which now, in the mounting, fixes the element into position.

U.S. Pat. No. 5,607,426 shows another solution for the polyaxial positioning of a fixation element. There is also at least one opening provided in the plate, which defines a mounting, in which a two-part insert may be inserted, the outer portion of which exhibits external threading which is able to engage with an interior threading in the plate provided on the side away from the bone. On the side near the bone, the plate is equipped with a conical tapering of the opening. Against this conical tapering the complementarily-shaped inner portion of the insert is supported. The inner portion of the insert has multiple slits, is hollow, and is equipped to hold a spherical head of the fixation element. Thus the fixation element may be polyaxially oriented. The screwing in of the outer part of the insert causes it to press on the inner part of the insert, which, as a consequence of its displacement in a perpendicular direction to the plate surface through the conical tapering, reduces the hollow space and thus fixes the spherical head of the fixation element in its position. It is clear that the polyaxial fixation of the spherical head of the fixation element must occur first and may be effected through the insertion of a tool in a groove provided in its head.

SUMMARY OF THE INVENTION

The invention has as one aspect improving a device of the type described in such a way that it is simpler, faster and more secure for the surgeon to handle.

This objective is achieved pursuant to the invention by the fact that the insert consists of two insert elements with a through bore wherein the first insert element exhibits the spherical outer shape, which allows its polyaxial rotation in the mounting. Additionally, the first insert element exhibits a central inner hollow space in which the second insert element may be inserted. The first insert element exhibits at least one slit of such a type that in an axial displacement of the two insert elements against each other the first insert element may be at least partially spread out in the plate, in order to block the position and orientation of the fixation element polyaxially when inserted in the device.

Through the fact that a two-part insert element is provided, a polyaxial locking may be secured in a simple manner, without this necessitating a higher expenditure in the insertion of such specially-designed bone plates.

PRELIMINARY DESCRIPTION OF THE DRAWINGS

The invention will now be described in two embodiments referencing the drawings. They show:

DETAILED DESCRIPTION

Figure 1:
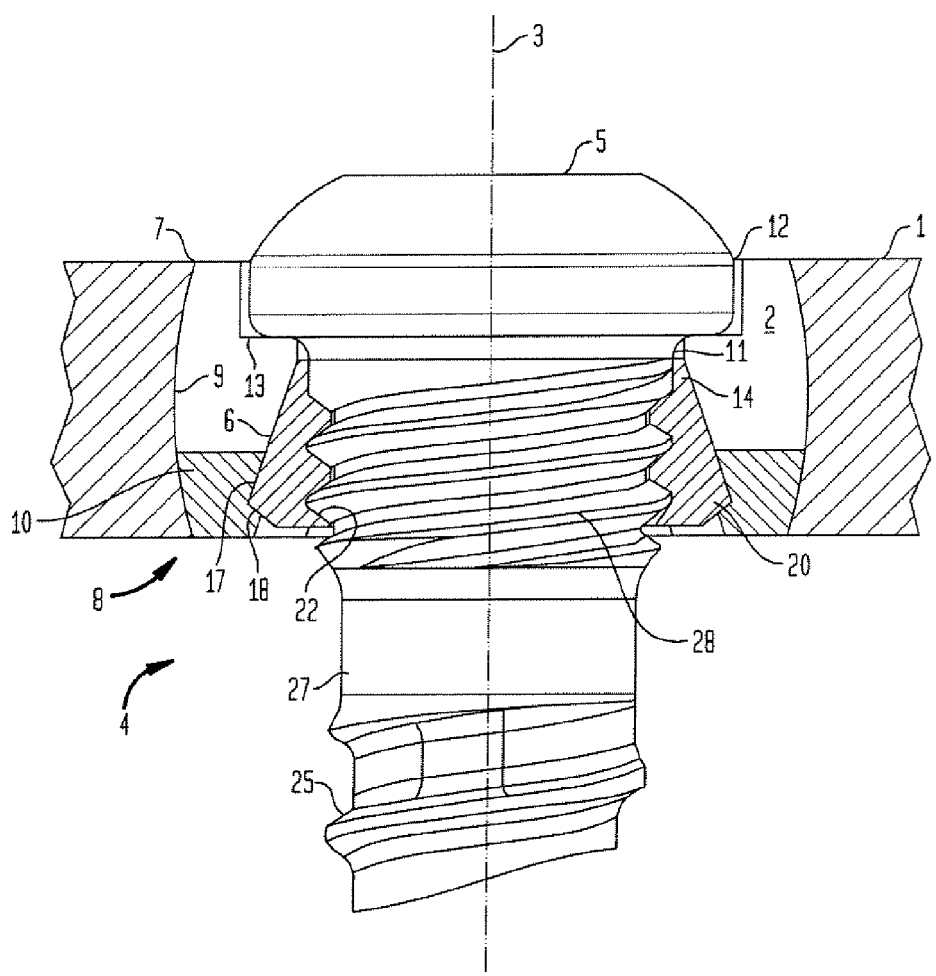
FIG. 1 is a sectional side view of a first embodiment of the device.

FIG. 1 shows a sectional side view of a first embodiment of the device. A plate identified as 1 is generally intended for implantation on a bone. Plate 1 normally has a number of holes 2 at an angle to its principle plane. The main axis of the holes 2 is identified as 3. The bone material is in the area marked 4 when inserting the device. Instead of the plate 1, one may also speak more generally of a load-bearing element, since besides plates, other load-bearing element such as, for example, rods, in particular, may be provided for the insertion of the invention.

The holes 2 may (not illustrated) be shaped as hollow cylinders near the opening, so that outer walls parallel to the main axis 3 result. The openings themselves may be rounded off or shaped so as to form spheres facing outward. These parallel outer walls may, however, also be shaped differently, for example with the opening widening conically, or narrowing conically, to name only two simple rotation-symmetrical possibilities. What is essential is the existence of projections 7 or 8. This means that between these projections 7 or 8 a mounting 9 is created, which is shaped like a hollow sphere. The diameter of this hollowed out mounting 9 is larger than the cylindrically-shaped space formed by the projections 7 or 8. This assures that flange-like rotating projections 7 or 8 exist, that securely hold an insert element 10, which is at least in some parts spherical, in the mounting 9.

This first spherical insert element 10 can then turn freely around its spherical mid-point, which lies in the axis 3, which is represented in FIG. 1 by the perpendicular orientation of the first insert element 10. The first insert element 10, however, cannot fall out of the mounting 9.

Figure 2:
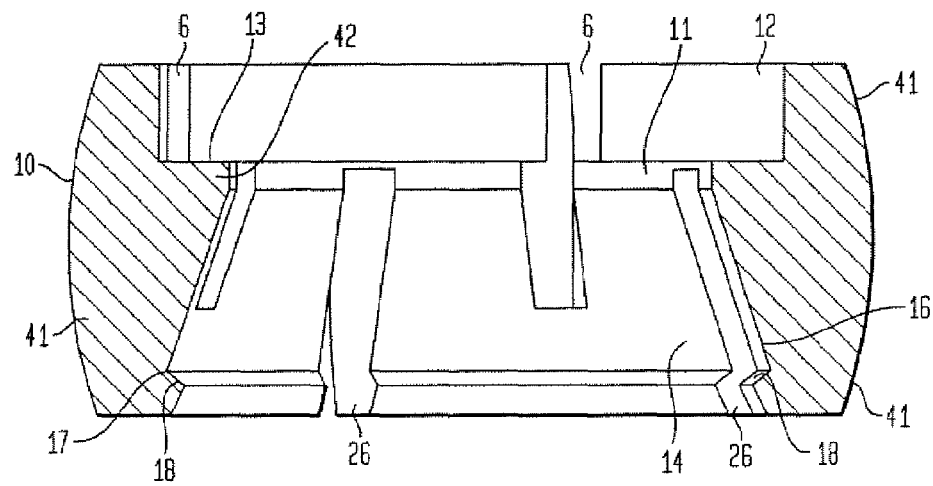
FIG. 2 is a sectional view of the first insert element from FIG. 1.

The first insert element 10 here has partial slits at four locations at a distance of 90 degrees reciprocally from above and below, which may be seen more clearly in the detailed drawing of FIG. 2. The same characterizing features are given the same reference numbers in all drawings. The characterizing features of the first insert element 10 to be described below in connection with FIG. 1 may also be seen in the detailed drawing thereof in FIG. 2. Two slits 6 are made from above, and two slits 6 from below in the first insert element 10.

In FIG. 1 the cutting plane lies in the two opposing open slits 6, above. The first insert element 10 is equipped along axis 3 with a through bore 11 for the passage of a fixation element 5, such that the passage widens on the side away from the bone into a mounting 12 for a fixation element head, and thus defines a shoulder 13, on which the fixation element head may be supported. The shoulder 13 spans a plane that runs perpendicular to the main axis 3 of the first insert element 10.

On the side near the bone, the first insert element 10 is equipped along axis 3 with a similarly widened hollow space 14 for the acceptance of a second insert element 20.

The hollow space 14 of the first insert element 10, provided to accept the second insert element 20, it widens in the direction of the end 4 near the bone and forms a conical wall surface 16. In place of a cone that opens up, another form may be selected, preferably one that is rotation-symmetrical to axis 3.

On the end of the conical wall surface 16 near the bone a bend (or alternatively a continuous transition through a rounding) 17 is provided, with which the hollow space 14 of the first insert element 10 goes into a cone that closes in on itself with a wall surface 18. The wall surface 18 may also be seen as a part of an inward-projecting rotating lug. Here it is sufficient for the holding function if only partial areas of the perimeter exhibit the said inward-projecting lugs 18.

Figure 3:
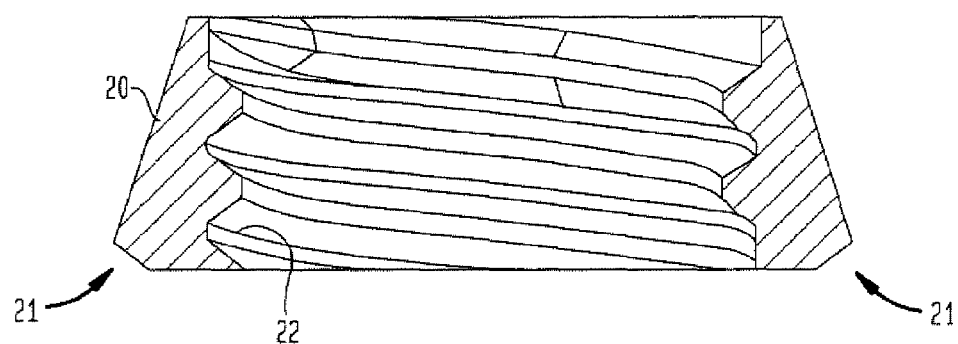
FIG. 3 is a sectional view of the second insert element from FIG. 1.

The second insert element 20 is essentially shaped to be complementary to the hollow space 14 of the first insert element 10, so that it can be taken up, with some play, in the hollow space 14 of the first insert element 10. FIG. 3 shows a sectional view of the second insert element from FIG. 1, in which the largest section 21 of the second insert element 20 may be more clearly seen, which lies in the area of the passage 17 of the first insert element 10. Through the wall surface 18 of the first insert element 10 the second insert element 20 is held in the first insert element 10.

Referring to FIG. 3, the second insert element 20 does not have slits and preferably is not compressible. It has a continuous inner-threaded bore 22 into which fixation element 5 may be screwed.

The device functions as follows: Plate 1 is placed on the bone area 4, is made ready in the holes 2, in which the polyaxial fixation is provided, with the two insert elements 10 and 20 inserted. The fixation element 5, for example a screw, is set down, directly or through a guide, and positioned so that the main axis 3 of the screw 5 is aligned with the main axis of the two insert elements 10 and 20. Through the spherical outer shape of the first insert element 10, a broad range of angles may be selected. The screw 5, when screwed in, at first engages with its outer threading 25, later to be anchored in the bone, into the inner threading 22 of the second insert element 20 and then in the bone material 4. In this way the screw head moves from the side away from the bone towards the plate 1 and the first insert element 10. The diameter of the bone screw 5 and the associated threading size may be selected such that the said first outer threading 25 of the bone screw 5 goes through the first insert element 10 without touching it. After a cylindrical transition area 27 the screw has a second outer threading 28. The second outer threading 28 is cylindrical and engages with the threading 22 of the second insert element 20.

Aside from the directional guiding of the screw 5 in the second insert element 20 an additional fixing of the direction and orientation occurs in the moment when the head of the fixation element 5 enters into the hollow space 12, since then side walls of the first insert element 10 confirm the previously set orientation in the first insert element 10 as well, to the extent that the diameter of the shaft and the threading 27 and 28 of the bone screw 5 are sufficiently great. Then comes the moment when the fixation element 5 is screwed in far enough that the head lies on the shoulder 13. From this point further turning of the fixation element 5 effects an axial movement of the second insert element 20 along the axis 3 toward the hollow space 14. In this way the conical surfaces 16 of the two insert elements toward one another and the inner, inflexible, second insert element spreads the flexible first insert element 10 apart, so that its spherical outer surfaces at least partially press against the wall of mounting 9. In this way it is possible, by simply pulling tight the fixation element 5, to set the previously adjusted polyaxial orientation and to confirm it.

Advantageously, the plate 1 and the insert elements 10 and 20 are made of medical steel or titanium or another material used in medicine technology. In particular, PEEK may be used as a material, which—in addition to other materials— also allows another advantageous embodiment of the first insert element 10. Then this first insert element 10 can be designed without slits, since, through the choice of materials it is in itself flexible. Such an insert element 10 is thus advantageously strengthened with carbon fibers. What is essential is that the first insert element can be deformed elastically, so the type and number of slits and/or the selection of materials are only two examples of possible embodiments. The said deformability or flexibility must allow a spreading out of the first insert element 10 in a radial direction with respect to the mounting 9. In the embodiment portrayed, the mounting 9 is a hollow sphere centered in the thickness of the plate 1.

Figure 4:
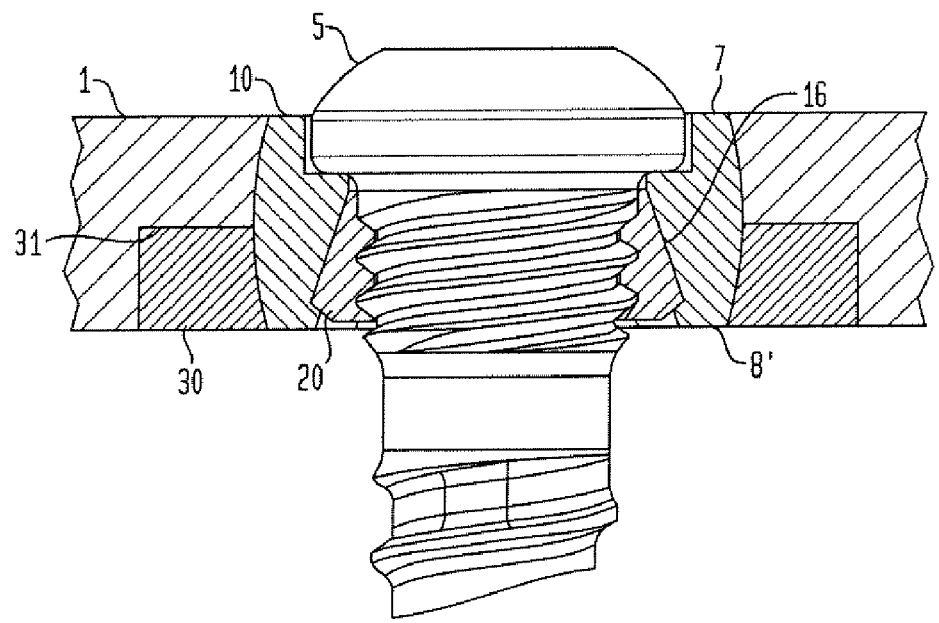
FIG. 4 is a sectional side view of a first modified form of the first embodiment of the device.
Figure 5:
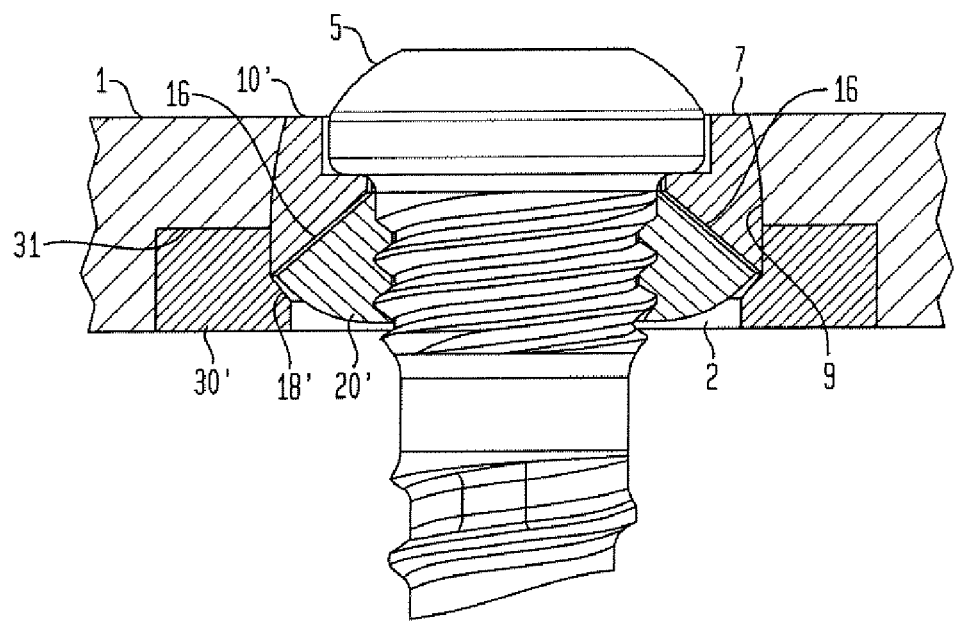
FIG. 5 is a sectional side view of a second modified form of the first embodiment of the device.

FIGS. 4 and 5 show sectional side views of two modified forms of the first embodiment of the device. The area of the first and second insert elements 10 and 20 is designed the same way as the embodiment represented in FIG. 1 through 3. As stated above, it is essential that the insert is held in the mounting 9, which is assured by means of the rotating projections 7 or 8 here in FIG. 1. These are the edges of the mounting 9 in FIG. 1 near the upper surface of the plate that, due to their hollow sphere form, have a smaller diameter than the depth of the mounting 9 itself.

This requires an exertion of force in inserting the insert.

FIG. 4 shows a design in which in the area near the bone, plate 1 exhibits a ring-shaped recess 31. The insert elements 10 and 20 are then first inserted in the mounting 9 and set in such a way that a third insert element 30 may subsequently be inserted as a ring in the corresponding recess 31 in the plate 1. Here the fixing action may be provided by pressing, screwing, bonding or another process commonly used in medical technology. This third insert element 30 then is provided with a spherical inner surface, which continuously fills in the mounting 9 of the plate 1, so that the first insert element may now be supported on the side near the bone before the implantation by the rotating tapered edge 8'. The implantation itself takes place in the same way as with the first embodiment, i.e. through the interaction of both the first and the second insert elements 10' and 20' on the complementary surfaces 16, without the third insert element 30 exercising an essential function here. It only takes up the forces exerted on the half near the bone in spreading out the first insert element 10.

For the description of the first insert element 10' according to the second modification of the first embodiment, reference is made to the description of FIG. 1. The difference between the two first insert elements 10 and 10' consists of the fact that the first insert element 10' according to this modification has no area 17, which exhibits a bend or a continuous transition through a rounding of a widening section into a tapering section. Rather, the conical wall surface 16 ends or may, for example, transition into a surface parallel to the principle plane of the plate 1.

The second insert element 20', on the other hand, exhibits an area of large diameter. In this way, the first insert element 10' and the second insert element 20' may be freely inserted from the underside into opening 2 of plate 1. They are positioned in mounting 9 by means of a third insert element 30', which is inserted as a ring in a corresponding recess 31 in the plate 1. In this way, the fixing may be provided by pressing, screwing, bonding or another process commonly used in medical technology. This third insert element 30' then is equipped with a conical surface 18' tapering toward the bone 4, against which the second insert element 20' may be supported before the implantation. The implantation itself takes place in the same way as with the above-cited embodiments, i.e. through the interaction of both the first and the second insert elements 10 and 20' on the complementary surfaces 16.

In place of the complementary surfaces 16 shown in the drawings as conical surfaces, other surface forms that allow a frictional connection may be provided, which may tighten against each other, if a fixation element is pushed forward by the insert elements 10' and 20'.

In this way, both insert elements 10 and 20 or 10' and 20' are each held firmly against the against the spherical inner walls of the plate 1 through spreading out of the side areas 41 (FIG. 2) of the first insert element 10, 10', which happens as a result of the axial pressure of the underside of the fixation element head on the shoulder 13 and against the central area 42 of the first insert element 10, 10'. This holding action is exerted by the axial counter-movement of the second insert element 20 or 20' in the direction of its longitudinal axis 3, which thus spreads the wing areas 41, the inner surfaces 16 of which engage in a grip complementary to the tapering of the central area 42 with the corresponding surfaces of the second insert element 20 or 20'.

Figure 6:
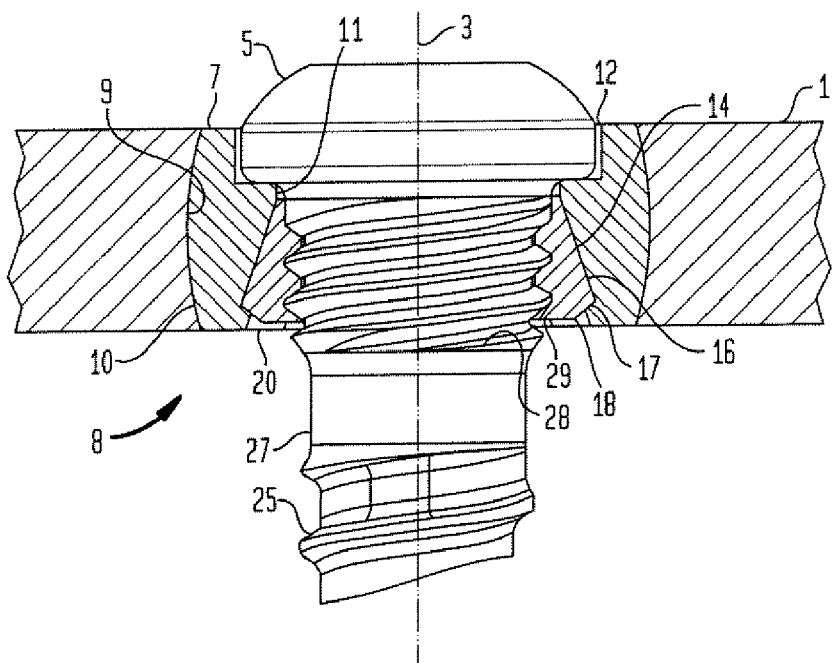
FIG. 6 is a sectional view in another plane of the first insert element of the first embodiment according to FIG. 1.

FIG. 6 shows a side view cut in another plane of the first insert element 10 of the first embodiment according to FIG. 1, such that the cut goes through the solid material of the first insert element 10 and thus no slits are visible. This figure therefore corresponds to an embodiment with a first insert element that is in itself flexible, for example, one made of PEEK.

Alternatively to the threading 22, the second insert element 20 may also be provided with a smooth inner boring, so that there is no direct contact between the screw 5 and the second insert element 20. Then the function of the axial movement of the second insert element 20 can be realized through underside 29 of the second insert element 20 being guided correspondingly closer to the bone, as when placed in the lower position presses against the first insert element 10 and spreads it.

Figure 7:
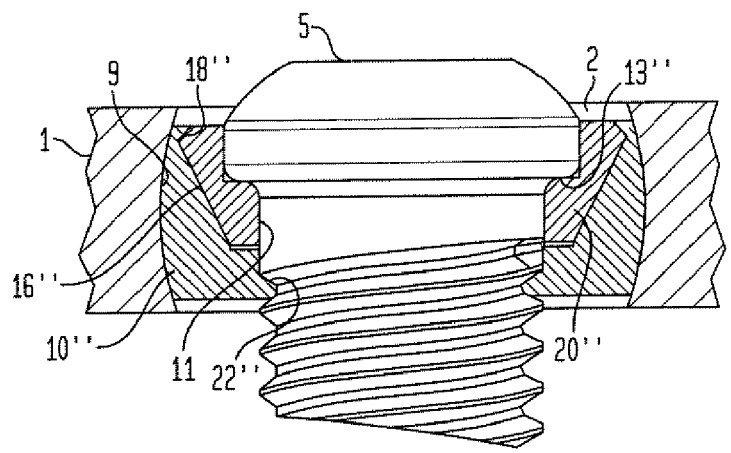
FIG. 7 is a sectional side view of a second embodiment of the device.

FIG. 7 finally shows a sectional side view of a second embodiment of the device. The same characterizing features appearing in the figures are always given the same reference numbers. Here the shoulder 13" is provided for support in the inner insert element, which is pressed by means of the head of the screw 5 against the outer insert element (and spreads it). For this to succeed, inner threading 22" is provided in the outer insert element. The design of the lug 18" and the conical engagement surfaces 16' can be executed as in the first embodiment.

The invention claimed is:

1. An implantable orthopedic device comprising a load-bearing plate, with at least one polyaxially-oriented fixation element, the load-bearing plate has at least one opening having a part-spherical inner surface for the passage of said at least one polyaxially-oriented fixation element, and first expandable insert, which may be inserted into said opening, the first expandable insert having a part-spherical outer shape that is complementary to the inner part-spherical shape of the opening to allow a polyaxial rotation of the insert in the opening, the first expandable insert having a central through-bore extending along an axis for accepting a body of the fixation element and allowing the polyaxial rotation of the same and further comprising a second insert for holding the first insert in the opening the first expandable insert element having a central recess surrounding the through-bore thereof for receiving the second insert, the first expandable insert element is capable of being expanded, by relative displacement of the first and second insert elements, the first expandable insert having two slits extending partially through the first expandable insert from a first side and two slits extending partially therethrough from a second side of the first insert; the first and second sides of the first expandable insert element extending transverse to the direction of the axis and the implantable orthopedic device further comprising a means for holding the first and second inserts in the opening which includes a third ring-shaped insert that is inserted in a recess in the plate surrounding the at least one opening and extending part way through a thickness of the plate from a bone contacting side of the plate and into contact with the first expandable insert.

2. The device as claimed in claim 1, wherein the first expandable insert is positioned adjacent a side of the plate opposite the bone contacting side and has a stop shoulder around the central through-bore thereof for contacting a head of the fixation element.

3. The device as claimed in claim 2, wherein a through-bore of the second insert at least partially includes an inner threading for engaging an outer threading of the fixation element.

4. The device as claimed in claim 2, wherein the central recess in the first expandable insert tapers inwardly towards the head of the fixation element and the second insert has a tapering shape that is complementary to the taper of the central recess of the first insert.

5. The device as claimed in claim 3, wherein the second insert has a through bore and has on a side opposite the bone contacting surface of the plate, a shoulder around the central through-bore for engaging the head of the fixation element.

6. The device as claimed in claim 1, wherein the central recess in the first expandable element is tapered and widens in the direction of the bone contacting surface of the bone plate and second insert is designed with a tapered shape that is complementary to the recess in the first insert.

7. The device as claimed in claim 1 wherein the third ring-shaped insert element exhibits an inwardly-directed shoulder that can be brought into engagement with the second insert element.

8. The device as claimed in claim 1, wherein the means for holding the second insert in the at least one opening includes lug on an end of the first expandable insert adjacent the plate bone contacting surface.

9. A locking system for a polyaxial bone screw mounted in a bone plate comprising:
a bone plate having an aperture with a part-spherical wall;
a bone screw having a head and a threaded shank;
an insert mounted in said aperture in said bone plate having an expandable first part with a part-spherical outer surface for engaging said part-spherical wall of said aperture, and a through-bore for receiving said bone screw along an axis, said insert having a second part slidably mounted within said first part and having a through-bore aligned with said through-bore of said first part, said first part having a tapered recess surrounding at least a part of said through-bore for engaging a tapered outer surface on said second part surrounding said through-bore thereof, one of said first or second parts engaging said thread on said bone screw shank and the other of said first or second parts engaging said bone screw head whereby relative axial movement of said first and second parts causes said first part to expand against said aperture wall and lock said polyaxial bone screw at a desire axial orientation with respect to said bone plate, the first part having two slits extending partially through the first part from a first side and two slits extending partially therethrough from a second side of the first part; the first and second sides of the first part extending transverse to the direction of the axis wherein the first and second inserts are held within the aperture by a third ring-shaped insert part that is insertable from a bone contacting side of the plate in a recess in the plate surrounding the aperture of the bone plate and extending part way through a thickness of the plate from the bone contacting side and into contact with the first insert part.

10. The locking system as claimed in claim 9, wherein the first insert part is positioned adjacent a side of the plate facing away from the bone and has a shoulder around the through-bore, which shoulder is provided as a stop for the head of the bone screw, the shoulder is arranged adjacent a central section of the first insert part connected to a tapered recessed surface surrounding said through-bore in said first part and the recess open towards the plate bone-contacting surface.

11. The locking system as claimed in claim 9, wherein the through-bore of the second insert part includes an inner thread for engaging an outer thread on the shank of the bone screw.

12. The locking element as claimed in claim 10, wherein the tapered recess of the first insert part tapers towards the head of the bone screw and the second insert part has an outer tapered surface that is complementary to the tapered recess.

13. The locking system as claimed in claim 11, wherein the second insert part, on a side opposite the plate bone-contacting surface has a shoulder around the through-bore which engages the head of the bone screw.

14. The locking system as claimed in claim 13, wherein the tapered recess of the first part widens in the direction of the plate bone contacting surface and the second insert element has a tapered shape that is complementary to the tapered recess.

15. The locking system as claimed in claim 9, wherein said third insert part has an inwardly-directed shoulder that can be brought into engagement with the second insert part.

16. The locking system as claimed in claim 9, wherein the first insert part includes a lug mounted on the end of the first insert part adjacent the plate bone-contacting surface.

* * * * *

UNITED STATES PATENT AND TRADEMARK OFFICE
CERTIFICATE OF CORRECTION

PATENT NO. : 7,686,837 B2  
APPLICATION NO. : 10/544323  
DATED : March 30, 2010  
INVENTOR(S) : André Gasser et al.

Page 1 of 1

It is certified that error appears in the above-identified patent and that said Letters Patent is hereby corrected as shown below:

Column 4, line 10, "spreads" should read --spread--.
Column 6, line 1, "and first" should read --and a first--.
Column 6, line 47, "and second" should read --and the second--.
Column 6, line 54, "opening includes" should read --opening includes a--.

Signed and Sealed this
Twenty-second Day of March, 2011

David J. Kappos
*Director of the United States Patent and Trademark Office*